United States Patent [19]

Lucchetti et al.

[11] Patent Number: 5,505,960
[45] Date of Patent: Apr. 9, 1996

[54] LIPOSOMAL PIROXICAM FORMULATIONS

[75] Inventors: Giovanni Lucchetti; Guiseppe Assogna, both of Rome; Pietro Bagnato, Latina, all of Italy

[73] Assignee: Janssen Farmaceutici S.p.A., Italy

[21] Appl. No.: 256,850

[22] PCT Filed: Feb. 4, 1993

[86] PCT No.: PCT/EP93/00272

§ 371 Date: Jul. 26, 1994

§ 102(e) Date: Jul. 26, 1994

[87] PCT Pub. No.: WO93/15718

PCT Pub. Date: Aug. 19, 1993

[30] Foreign Application Priority Data

Feb. 12, 1992 [EP] European Pat. Off. .............. 92200398

[51] Int. Cl.⁶ .................................................. A61K 9/127
[52] U.S. Cl. ............................................................ 424/450
[58] Field of Search ...................... 424/450; 264/4.1–4.3

[56] References Cited

U.S. PATENT DOCUMENTS

| | | | |
|---|---|---|---|
| 3,699,230 | 10/1972 | Beauchamp | 424/272 |
| 4,082,881 | 4/1978 | Chin | 424/241 |
| 4,963,297 | 10/1990 | Madden | 264/4.3 |

FOREIGN PATENT DOCUMENTS

| | | |
|---|---|---|
| 0215423 | 3/1987 | European Pat. Off. . |
| 249561 | 12/1987 | European Pat. Off. . |
| 253619 | 1/1988 | European Pat. Off. . |
| 0260241 | 3/1988 | European Pat. Off. . |
| 0284588 | 9/1988 | European Pat. Off. . |
| 0427582 | 5/1991 | European Pat. Off. . |
| WO88/07871 | 10/1988 | WIPO . |

*Primary Examiner*—Gollamudi S. Kishore
*Attorney, Agent, or Firm*—Charles J. Metz

[57] ABSTRACT

The present invention relates to a topical liposomal formulation comprising piroxicam, a phospholipid, a solvent system for piroxicam and said phospholipid, water and conventional auxiliary formulating agents, and a method of preparing said formulation.

8 Claims, No Drawings

LIPOSOMAL PIROXICAM FORMULATIONS

CROSS-REFERENCE TO RELATED APPLICATIONS

This application is based upon PCT Application Serial No. PCT/EP 93/00272, filed Feb. 4, 1993, which claims priority from European patent application Serial No. 92.200.398.3, filed Feb. 12, 1992.

The present invention relates to a topical liposomal formulation comprising piroxicam, a phospholipid, a solvent system for piroxicam and said phospholipid, water and conventional auxiliary formulating agents, and a method of preparing said formulation.

JP-61/172,833 discloses formulations comprising non-steroidal anti-inflammatory drugs such as indomethacin and piroxicam, with phospholipids. Said compositions are not made up of liposomes, however.

EP-0,249,561 and EP-0,260,241 disclose particular liposomal formulations for systemic administration of active ingredients, including piroxicam.

EP-0,253,619 describes a convenient method for preparing single bilayered liposomes containing encapsulated active ingredients.

Piroxicam is an analgesic, anti-inflammatory and antipyretic drug which is sparingly soluble in aqueous and/or alcoholic media. This property considerably hampers the development of effective topical piroxicam formulations. Classic topical formulations usually comprise a rather large amount of piroxicam, mostly dispersed, in order to deliver a sufficient amount of the active ingredient to the area that is treated. The problem has now been solved by using an especially designed organic solvent system.

The present liposomal piroxicam formulation penetrates rapidly and deeply in epithelial tissues and shows excellent retention of the active ingredient therein. The efficacy of the composition is similar to that of classic cream formulations wherein piroxicam is dispersed, although the concentration of piroxicam in the present formulations often is considerably lower than the concentration of piroxicam in said classic cream formulations. The present formulation is stable and in particular does not show the disadvantage of crystallization of the sparingly soluble active ingredient piroxicam.

The present invention provides a topical liposomal formulation comprising piroxicam, a phospholipid, a solvent system for piroxicam and said phospholipid, water and conventional auxiliary formulating agents, characterized in that said composition comprises as a solvent system dimethylisosorbide and tetraglycol. The use of said solvent system in topical liposomal formulations is novel.

The present composition is preferably in the form of single bilayered liposomes, in particular liposomes having a size ranging from 100 to 1000 nm, more in particular from 100 to 500 nm. In general, the stability of the liposomal formulation increases as the size of the single bilayered liposomes decreases. Single bilayered liposomes, also referred to as unilamellar vesicles, consist of a single bilayer of suitable amphophilic molecules such as phospholipids which encapsulate an aqueous phase and which are separated from each other by an aqueous phase.

Hereinafter, the amounts of each of the ingredients in the present composition are expressed as percentages by weight based on the total weight of the formulation. Similarly, ratios are intended to define weight-by-weight ratios.

Suitable phospholipids for use in the present composition are, for example, phosphatidyl cholines, ethanolamines and serines, sphingomyelins, cardiolipins, plasmalogens, phosphatictic acids and cerebrosides, in particular those which are soluble together with piroxicam in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation can range from about 10 to about 30%, preferably from about 15 to about 25% and in particular is about 20%.

Lipophilic additives may be employed advantageously to modify selectively the characteristics of the liposomes. Examples of such additives include, for example, stearylamine, phosphatictic acid, tocopherol, cholesterol, cholesterol hemisuccinate and lanolin extracts; cholesterol being a lipophilic additive of choice. The amount of lipophilic additive used can range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10.

Said phospholipid, lipophilic additive and the active ingredient piroxicam are employed in conjunction with a non-toxic, pharmaceutically acceptable organic solvent system which can dissolve said ingredients. The organic solvent system used in the present formulation is of crucial importance. Said solvent system not only must dissolve the active ingredient piroxicam completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%, in particular about 12 to about 20% and preferably about 15%. In said solvent system, the ratio of the amount of dimethylisosorbide to the amount of tetraglycol can range from about 2:1 to about 1:3, in particular from about 1:1 to about 1:2.5 and preferably is about 1:2. The amount of tetraglycol in the final composition thus can vary from 5 to 20%, in particular from 5 to 15% and preferably is approximately 10%. The amount of dimethylisosorbide in the final composition thus can range from 3 to 10%, in particular from 3 to 7% and preferably is approximately 5%.

The term "organic component" as used hereinafter refers to mixtures comprising said phospholipid, lipophilic additives and organic solvents.

The active ingredient piroxicam is dissolved in the organic component. It may be advantageous to use micronized forms of the active ingredient to facilitate its dissolution. The amount of active ingredient in the final formulation ranges from 0.1 to 0.6%, in particular from 0.4 to 0.5% and preferably is approximately 0.5%. In addition, other ingredients such as anti-oxidants may be added to the organic component. Examples thereof include tocopherol, butylated hydroxyanisole, butylated hydroxytoluene, ascorbyl palmitate, ascorbyl oleate and the like.

The aqueous component of the present formulation comprises mainly water and may contain various additives such as electrolytes, buffer systems, preservatives and the like. Suitable electrolytes include metal salts, in particular alkali metal and earth alkaline metal salts such as, for example, calcium chlorides, sodium chloride, potassium chloride, preferably sodium chloride. The concentration of the electrolytes may vary over a wide range and depends on the nature and the concentration of each of the ingredients in the final formulation and should be sufficient to stabilize the liposomal membranes. In the present composition the amount of sodium chloride can range from 0.05 to 0.2% and in particular is about 0.1%. Buffer systems comprise mixtures of appropriate amounts of an acid such as phosphoric, succinic, or preferably citric acid, and a base, in particular sodium hydroxide. Said buffer systems should maintain the pH of the formulation within the range of 5 to 7, preferably within the range of 5 to 6.5 and especially within the range of 5.5 to 6. Preservatives which can be employed in the present composition to prevent degradation by microorganisms comprise benzoic acid, methylparaben and propylparaben. Preferably, methylparaben and propylparaben are used in an amount of approximately 0.2% and 0.02% respectively. It is especially advantageous to add to the aqueous component a chelating agent such as sodium or disodium edetate in order to prevent the oxidative degradation of the phospholipid in the final formulation by metal ions. An effective amount of for example disodium edetate ranges from 0.05% to 0.25% and in particular is approximately 0.15%.

Preferred compositions comprise by weight based on the total weight of the composition:

(a) 0.1 to 0.6% piroxicam;

(b) 10 to 30% phospholipid;

(c) 0.5 to 8% cholesterol;

(d) 3 to 10% dimethylisosorbide;

(e) 5 to 20% tetraglycol;

(f) buffer to maintain the pH of the composition within the range of 5 to 7;

(g) sufficient electrolytes to stabilize the liposomal membranes;

(h) sufficient dermatologically acceptable preservatives to prevent degradation of the composition;

(i) 0.5 to 1.5% thickening agent; and (j) water.

Particularly preferred compositions are those wherein:

the amount of piroxicam is 0.4 to 0.5%;

the amount of phospholipid is 15 to 25%;

the amount of cholesterol is 1.5% to 4%;

the amount of dimethylisosorbide is 3 to 7%;

the amount of tetraglycol is 5 to 15%; and the amount of thickening agent is 1.5%.

The most preferred composition comprises approximately by weight based on the total weight of the composition:

(a) 0.5% piroxicam;

(b) 20% phospholipid;

(c) 2% cholesterol;

(d) 5% dimethylisosorbide;

(e) 10% tetraglycol;

(f) 0.06% sodium hydroxide and 0.1% citric acid;

(g) 0.1% sodium chloride;

(h) 0.2% methylparaben, 0.02% propylparaben, 0.01% butylated hydroxytoluene, and 0.15% disodium edetate;

(i) 1.5% hydroxypropyl methylcellulose; and (j) water.

The liposomal piroxicam formulation of the present invention can preferably be prepared by (a) heating the phospholipid and the organic solvent system to about 60° to 80° C., preferably to about 70° to 75° C. in a first vessel, dissolving the active ingredient therein, adding thereto the auxiliary formulating agents, and stirring the mixture until complete dissolution is obtained;

(b) heating pan of the water to 90°–95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component;

(c) transferring the contents of the first vessel by means of a vacuum directly into the aqueous component, while homogenizing the thus obtained combination with a high performance mixing apparatus, in particular a high-shear mixer; and (d) adding a thickener to the resulting mixture by means of a vacuum while further homogenizing.

Preferably, the aqueous component is placed in a suitable vessel which can be equiped with a homogenizer and homogenization is effected by creating great turbulence during the injection of the organic component. Any mixing means or homogenizer which exerts high shear forces on the mixture may be employed. Generally, a mixer capable of speeds from about 1,500 to 20,000 rpm, in particular from about 3,000 to about 6,000 rpm may be employed. Suitable thickening agents for use in process step (d) are for example, xanthan gum, hydroxypropyl cellulose, hydroxypropyl methylcellulose or mixtures thereof, cellulose derivatives being preferred. The amount of thickening agent depends on the nature and the concentration of the other ingredients and in general ranges from about 0.5 to 1.5%, and in particular is approximately 1.5%.

In order to prevent degradation of the materials used during the preparation of the liposimal formulation, it is advantageous to purge all solutions with an inert gas such as nitrogen or argon, and to conduct all steps under an inert atmosphere.

Liposomes prepared by the above described method usually contain most of the active ingredient bound in the lipid bilayer and separation of the liposomes from unencapsulated material is not required. The single bilayered liposomes can conveniently be employed directly or they may also be employed in combination with other suitable pharmaceutically acceptable carders for topical administration.

The above described liposomal compositions are particularly useful for the topical treatment of subjects suffering from soft-tissue injuries and sprain pathologies of traumatic origin, in particular for treating acute forms of said problems. Typical pathologies are injuries of the joints such as the knee, ankle, wrist, elbow, shoulder and back. The present liposomal compositions offer excellent relief of both slight and severe pain. The piroxicam containing compositions are applied topically to the area to be treated at regular intervals, as needed, generally once, twice or thrice a day. The duration of the treatment will depend on the nature, extent and severity of the condition to be treated as well as the frequency of applying the composition.

The following examples are intended to illustrate the scope of the present invention in all its aspects and not to limit it thereto.

EXAMPLE 1

| Ingredient | Quantity, mg/g of cream |
| --- | --- |
| piroxicam | 5.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| butylated hydroxytoluene | 0.1 |
| disodium edetate | 1.5 |
| sodium chloride | 1.0 |
| hydroxypropyl methylcellulose | 15.0 |
| sodium hydroxide | 0.6 |
| citric acid | 1.0 |
| purified water, USP | 603.6 |

Procedure

1. Heat the soya lecithin, tetraglycol and dimethyl isosorbide to about 70°–75° C. Dissolve the piroxicam, cholesterol and butylated hydroxytoluene in the heated mixture. Stir until complete dissolution is obtained.

2. Heat about one third of the water to 80°–95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution.

3. Transfer the mixture resulting from step 1 into the mixture resulting from step 2 by means of a vacuum, while homogenizing the combination with a high-shear mixer until a homogeneous product is obtained.

4. Add the hydroxypropyl methylcellulose into the mixture resulting from step 3 by means of a vacuum while homogenizing with a mixer.

The homogenizer was a Silverson high-shear mixer operating at approximately 3000 rpm. The flow rate during the transfer steps was about 0.5 l/min. Single bilayered liposomes were formed. The white lipogel cream resulting from step 4 can conveniently be filled in suitable containers such as tubes, e.g. PVC-covered aluminum tubes.

Clinical example

20 Patients, aged 26–38, were treated with the cream formulation of example 1. All were affected by acute soft-tissue injury and acute sprain pathology of traumatic origin (extra articular rheumatism); the most frequent pathologies being injury of the knee, ankle, shoulder and of the back. The duration of the treatment lasted 10 days and consisted of applying the cream twice a day to the affected area.

The clinical evaluation of the cream was based on parameters such as pain, swelling, limitation of active and passive movements and on an overall assessment of the efficacy and tolerance.

The obtained results were considered excellent and good in 89% of the patients. In particular, both patients with light and severe pain reported feeling much better after the treatment.

The tolerance to the drug formulation was very good. None of the patients experienced side effects and all patients completed to clinical trial.

We claim:

1. A topical liposomal composition comprising piroxicam, a phospholipid, and a solvent system for piroxicam, characterized in that said solvent system consists essentially of dimethylisosorbide and tetraglycol.

2. A composition according to claim 1 wherein the liposomes are single bilayered liposomes.

3. A composition according to claim 2 wherein the phospholipid is lecithin.

4. A composition according to claim 3 wherein the amount of dimethylisosorbide and tetraglycol ranges from 8 to 30% by weight based on the total weight of the composition.

5. A composition according to claim 4 wherein the ratio of the amount of dimethylisosorbide to the amount of tetraglycol ranges from 2:1 to 1:3.

6. A composition according to claim 1 comprising by weight based on the total weight of the composition:
   (a) 0.1 to 0.6% piroxicam;
   (b) 10 to 30% phospholipid;
   (c) 0.5 to 8% cholesterol;
   (d) 3 to 10% dimethylisosorbide;
   (e) 5 to 20% tetraglycol;
   (f) buffer to maintain the pH of the composition within the range of 5 to 7;
   (g) sufficient electrolytes to stabilize the liposomal membranes;
   (h) sufficient dermatologically acceptable preservatives to prevent degradation of the composition;
   (i) 0.5 to 1.5% thickening agent; and
   (j) water.

7. A composition according to claim 6 wherein
   the amount of piroxicam is 0.4 to 0.5%;
   the amount of phospholipid is 15 to 25%;
   the amount of cholesterol is 1.5% to 4%;
   the amount of dimethylisosorbide is 3 to 7%;
   the amount of tetraglycol is 5 to 15%; and
   the amount of thickening agent is 1.5%.

8. A composition according to claim 7 comprising approximately;
   (a) 0.5% piroxicam;
   (b) 20% phospholipid;
   (c) 2% cholesterol;
   (d) 5% dimethylisosorbide;
   (e) 10% tetraglycol;
   (f) 0.06% sodium hydroxide and 0.1% citric acid;
   (g) 0.1% sodium chloride;
   (h) 0.2% methylparaben, 0.02% propylparaben, 0.01% butylated hydroxytoluene, and 0.15% disodium edetate;
   (i) 1.5% hydroxypropyl methylcellulose; and
   (j) water.

* * * * *